United States Patent [19]

Tschang et al.

[11] Patent Number: 4,551,482
[45] Date of Patent: Nov. 5, 1985

[54] MACROPOROUS, HYDROPHILIC ENZYME CARRIER

[75] Inventors: Chung-Ji Tschang, Bad Durkheim; Stefan Marcinowski, Ludwigshafen, both of Fed. Rep. of Germany

[73] Assignee: BASF Aktiengesellschaft, Fed. Rep. of Germany

[21] Appl. No.: 507,108

[22] Filed: Jun. 23, 1983

[51] Int. Cl.$^4$ .............................. C08J 9/36; C08J 9/40
[52] U.S. Cl. ...................................... 521/53; 435/180; 521/55; 521/149; 521/150
[58] Field of Search .................... 521/53, 55, 149, 150

[56] References Cited

U.S. PATENT DOCUMENTS

| | | | |
|---|---|---|---|
| 3,326,866 | 6/1967 | Haag | 521/53 |
| 4,141,857 | 2/1979 | Levy et al. | 252/430 |
| 4,235,973 | 11/1980 | Tschang et al. | 521/53 |
| 4,268,419 | 5/1981 | Rohrbach | 252/430 |
| 4,268,423 | 5/1981 | Rohrbach et al. | 252/430 |
| 4,490,487 | 12/1984 | Halcour et al. | 521/53 |

OTHER PUBLICATIONS

Klaus Mosbach, Ed., *Methods in Enzymology*, vol. XLIV, "Immobilized Enzymes", (1976), pp. v–ix.

Ichiro Chibata, Ed., Immobilized Enzymes, (1978), p. v.

G. Manecke et al., "Reaktive Trager auf der Basis von Polyethylenimin zur Immobilisierung von Enzymen", *Makromol. Chem.*, vol. 182, (1981), pp. 2641–2657.

P. Grunwald et al., "Application of Polyethylene Imine as Carrier Material for Enzyme Immobilization", *Naturwissenschaften* 68 (1981), pp. 525–526.

Akio Subitachi et al., "Immobilization of Plasminogen Activator, Urokinase, on Nylon", *Thrombos. Haemostas.* (Stuttg.), 1978, pp. 426–436.

J. Konecny et al., "Effects of Carrier Morphology and Buffer Diffusion on the Expression of Enzymatic Activity", *Biochimica et Biophysica Acta*, vol. 485, (1977), pp. 367–378.

*Primary Examiner*—Morton Foelak
*Attorney, Agent, or Firm*—Keil & Weinkauf

[57] ABSTRACT

A macroporous, hydrophilic enzyme carrier comprises a sulfonated polymer, charged with polyethyleneimine, of from 10 to 100% by weight of divinylbenzene, from 0 to 90% by weight of styrene and from 0 to 20% by weight of a copolymerizable monomer, the polyethyleneimine being neither crosslinked nor covalently bonded to the polymer.

5 Claims, No Drawings

MACROPOROUS, HYDROPHILIC ENZYME CARRIER

The present invention relates to macroporous, cross-linked and hydrophilic polymers and their use for immobilizing enzymes.

Immobilized, i.e., carrier-bound, enzymes are used, inter alia, in medical analysis and in the preparation of pharmaceutical products, optically active substances and foodstuffs, e.g. in the preparation of isoglucose. The advantages of using immobilized enzymes are that they can be re-used, they are easy to separate from the substrate or its solution, they are frequently highly stable and hence, under given conditions, have a longer life in comparison with the soluble form, contamination of the reaction products is avoided and it is possible to carry out continuous reactions in columns or similar reactors.

A large number of possibilities for immobilizing enzymes is known. A detailed summary is given, for example, in Methods in Enzymology, vol. XLIV, "Immobilized Enzymes", (Academic Press, 1976), and in Immobilized Enzymes (I. Chibata; Kodansha Ltd./John Wiley & Sons, 1978). A frequently described method of immobilization is adsorptive, ionic or covalent bonding of enzymes to organic or inorganic carriers, including those of natural origin.

Numerous carriers which have been prepared using polyethyleneimine have been described in recent years. In some cases, polyethyleneimine which has been provided with functional groups for covalent bonding of enzymes is used as the matrix (G. Manecke and S. Heydolph, Makromol. Chem. 182 (1981), 2641–2657 and P., Grunwald et al., Naturwissenschaften 68 (1951), 525–526). In other cases, polyethyleneimine covalently bonded to nylon is used to bond a maleic anhydride/vinyl methyl ether copolymer, which in turn effects covalent bonding of enzymes (A. Sugitachi et al., Thrombos. Haemostas. (Stuttgart), 39 (1978), 426–435). Finally, a third group of polyethyleneimine-containing carriers is based on inorganic materials which are partly enveloped in polymers and onto which the polyethyleneimine is applied and then cross-linked with an excess of glutaro-dialdehyde, diisocyanates or other polyfunctional reagents (J. Konecny and W. Voser, Biochim. Biophys. Acta 485 (1977), 367–378, German Published Application DAS No. 2,605,797 and U.S. Pat. Nos. 4,141,857, 4,268,419 and 4,268,423). All these carriers have the common factor that the polyethyleneimine present in or on them is covalently crosslinked. For this, an additional operation and, as can be seen from the above statements, toxic agents, e.g. diisocyanates, are required. Moreover, the carrier is moisture-sensitive when provided with enzyme-binding groups, such as isocyanates or maleic anhydride groups, and must be stored in the absence of water until used.

It is an object of the present invention to provide carriers which are extremely simple to prepare, and be used for permanent immobilization of enzymes of high enzymatic activity, substantially avoid toxic substances, present no handling problems in use, i.e. can be stored without particular safety measures, and have good mechanical and hydrodynamic properties.

The subject carriers are obtained by treating macroporous, crosslinked, sulfo-containing polymer particles with polyethyleneimine. Surprisingly, crosslinking of the polyethyleneimine can be omitted, as a result of which the bound enzymatic activity is increased, which was completely unpredictable.

The polymers are prepared by free radical polymerization and contain, in copolymerized form, from 10 to 100% by weight, preferably from 15 to 40% by weight, of divinylbenzene, from 0 to 90% by weight, preferably from 60 to 85% by weight, of styrene, which may also be mono-or polysubstituted by $C_1$–$C_4$-alkyl on the nucleus, and from 0 to 20% by weight, preferably from 0 to 10% by weight, of monomers which are copolymerizable with divinylbenzene and styrene, e.g. alkyl acrylates or methacrylates. It is also possible to incorporate small amounts (not more than 10% by weight) of water-soluble monomers, e.g. acrylic acid, methacrylic acid or vinylimidazole. Particularly preferred polymers consist of from 30 to 60% by weight of technical-grade divinylbenzene (containing about 50% of divinylbenzene, the remainder being predominantly ethylstyrene, together with, inter alia, small amounts of trivinylbenzene) and from 70 to 40% by weight of styrene.

The monomer (mixture) is polymerized by suspension polymerization with water as the external phase, a particle diameter of from 0.05 to 3 mm, preferably from 0.2 to 0.8 mm, being aimed for. The macroporosity of the polymer is produced by a pore-forming agent. Suitable pore-forming agents are liquids which do not interfere with the polymerization, are water-immiscible, dissolve the monomer but do no more than slightly swell the polymer, e.g. alkanes of 7 to 12 carbon atoms, preferably n-octane, or gasolines having a boiling point of not less than 100° C. The amount of pore-forming agent is from 50 to 400% by weight, based on the monomers. The upper limit of the amount of pore-forming agent is given by the mechanical properties of the polymer and depends on the particular pore-forming agent. It is essential to produce a pore volume of from 0.8 to 4 cm$^3$/g, preferably from 1.2 to 3.0 cm$^3$/g, measured by mercury porosimetry, with pores from $2.5 \times 10^{-5}$ to $2 \times 10^{31}$ $^3$ mm, preferably from $4 \times 10^{-5}$ to $5 \times 10^{-4}$ mm, in diameter. The pore-forming agent is washed out of the finished polymer with the aid of a low-boiling solvent, e.g. acetone, and the polymer is then dried. The preparation of macroporous bead polymers is known from, for example, British Pat. No. 849,122.

It would, of course, also be possible to carry out the polymerization as a block polymerization. However, this would have the disadvantage that the polymer would have to be subsequently comminuted and would then have poorer hydrodynamic properties because of the irregular shape of the particles.

To achieve a relatively high immobilized enzyme activity, it is advantageous to subject the surface of the polymer to subsequent mechanical treatment, as described in European Laid-Open Application EOS No. 49,385.

The surface of the polymer is sulfonated in a conventional manner using sulfuric acid or chlorosulfonic acid in order to render the polymer hydrophilic. Descriptions of sulfonation methods are to be found, inter alia, in D. Braun, H. Cherdron and W. Kern, "Praktikum der Makromolekularen Organischen Chemie", Dr. Alfred Hüthig Verlag, Heidelberg 1966, page 234; in Ullmanns Encyklopädie, 4th edition, Verlag Chemie, Weinheim-New York, Volume 13, page 301, and in Houben-Weyl, "Methoden der Organischen Chemie", Georg Thieme-Verlag, Stuttgart 1963, Volume XIV/2, page 682–685. Sulfonation is continued until the surface of the polymer is sufficiently acidic and hydrophilic for subsequent charging with polyethyleneimine.

The polyethyleneimine is applied in aqueous solution onto the sulfonated polymer. The molecular weight of the polyethyleneimine, which can be linear or branched, should be from 1,000 to 50,000, preferably from 30,000 to 45,000. In order to avoid mechanical damage to the polymer by osmotic effects, the polyethyleneimine should be added in several portions, the initial concentration of the solution being about 2% by weight, but in any case not more than 3% by weight. If ten times the amount of aqueous solution, based on the amount of sulfonated polymer, is used, the final concentration of polyethyleneimine in the solution is from 1 to 6% by weight. Optimum polyethyleneimine charging can easily be ascertained in preliminary experiments by determining the immobilizable enzymatic activity. The polyethyleneimine is applied at from 0° to 100° C., preferably at room temperature, over a period of from 1 to 12, preferably from 4 to 8, hours. Because the polyethyleneimine concentration is low, it is not necessary to use higher temperatures in order to reduce the viscosity of the solution. After the carrier has been charged with from 5 to 30% by weight, preferably from 10 to 20% by weight, of polyethyleneimine, it can be washed with water, but this is not absolutely necessary. The carrier can be stored in either the dried or the wet state until charged with enzyme.

Charging of the carrier with enzyme is effected using an aqueous enzyme solution, which may advantageously contain a buffer, depending on the enzyme. The enzyme concentration of the solution is from 1 to 100 mg/ml, and the charging time is from 1 to 80, preferably from 10 to 40, hours. The enzyme solution is at from 0° to 90° C., depending on the enzyme. After charging, the carrier is freed from excess enzyme by washing and is used as a heterogeneous catalyst with enzymatic activity in either batchwise or continuous operation, for example in a column. The storage life of the enzyme-charged carrier depends on the enzyme, but it is generally advisable to charge the carrier with the enzyme shortly before use.

It is assumed that the enzyme is ionically bound to the carrier, but in principle without other bonding mechanisms, with the exception of covalent bonding, being excluded.

The carrier is distinguished in that it is easy to handle since it neither is deactivated by moisture nor must be activated before use. It is capable of immobilizing a high enzymatic activity, has excellent hydrodynamic properties and is not attacked by microorganisms.

EXAMPLE 1

(A) Preparation of the macroporous bead polymer

A bead polymer was prepared by heating 50 g of styrene, 50 g of technical-grade divinylbenzene, 180 ml of n-octane, 1 g of lauryl peroxide, as a source of free radicals, 500 ml of water and 1 g of polyvinylpyrrolidone, as a suspending auxiliary, to 70° C. for 4 hours and then to 95° C. for 4 hours in a flask with a stirrer and reflux condenser, while passing in nitrogen. The polymer was washed in acetone, water and methanol in succession and then dried at 70° C. under reduced pressure. It was then sieved down to a particle size of from $3.1 \times 10^{-2}$ cm to $5 \times 10^{-2}$ cm. 25 g of this sieved polymer were then mechanically shaken vigorously in a 250 ml glass bottle for 3 hours, washed again with acetone, water and methanol and finally dried at 70° C. under reduced pressure.

(B) Sulfonation of the macroporous bead polymer 20 g of the polymer prepared in (A) were stirred with 300 ml of concentrated sulfuric acid at room temperature for 1 hour and then at 100° C. for 8 hours. Thereafter, the polymer was filtered off on a frit with suction, transferred first to half-concentrated sulfuric acid and then to water, washed thoroughly by changing the water several times and finally dried at 70° C. under reduced pressure. The yield was 31.5 g.

(C) Charging of the sulfonated bead polymer with polyethyleneimine 10 g of the polymer sulfonated in (B) were stirred in 90 ml of an aqueous solution containing 1.5 g of polyethyleneimine having a molecular weight of about 40,000 at room temperature for 2 hours. A further 1.5 g of polyethyleneimine, dissolved in 8.5 ml of water, were then added and stirring was continued for 4 hours. The carrier was filtered off on a glass frit with suction, washed with 100 ml of water and then dried at 70° C. under reduced pressure.

(D) Charging of the carrier with enzyme and determination of the immodbilized enzyme activity 0.2 g of carrier was introduced into 20 ml of a solution containing 100 mg of invertase (150 international units/mg) in 0.005 M aqueous sodium acetate solution of ph 5.3 and the mixture was shaken at room temperature for 21 hours. The carrier was then washed for two periods of 5 minutes and one period of 1 hour with in each case 50 ml of 0.0025 M aqueous sodium acetate solution of pH 5.3.

To determine the enzyme activity, i.e. the immobilized activity, the polymer was shaken in 50 ml of a solution containing 17.5 g of sucrose in 0.01 M aqueous sodium acetate solution of pH 5.3. Hydrolysis of the sucrose was determined polarimetrically.

The immobilized activity was found to be 45.3 g of sucrose per gram of carrier per hour.

Comparative Example—Carrier with crosslinked polyethyleneimine 10 g of carrier prepared as in Examples 1 (A) to (C) were stirred with 100 ml of a solution containing 10 g of Epikote 828 (Shell) in anhydrous acetone in a round-bottomed flask with a stirrer, reflux condenser and drying tube, filled with calcium chloride, at 50° C. for 5 hours. The carrier was then filtered off from the solution on a glass frit with suction and dried at 70° C. under reduced pressure. Charging of the carrier with invertase and subsequent determination of the bound invertase activity as described in Example 1 (D) resulted in an activity of 23.4 g of sucrose per g of carrier per hour. It can be seen here that the activity is lower than that for the carrier according to the invention.

EXAMPLE 2

0.5 g of carrier prepared as in Example 1 was introduced into a column of 1.6 cm diameter. A solution of 500 mg of β-fructosidase in 100 ml of 0.05 M sodium acetate buffer of pH 5.3 was then pumped in circulation through the column at room temperature at a rate of 100 ml/hour for 16 hours. 100 ml/hour of aqueous 0.05 M sodium acetate solution of pH 5.3 were then pumped through the column for 24 hours in order to remove non-bound enzyme. A solution of 350 g of sucrose/liter in 0.05 M aqueous sodium acetate solution of pH 5.3 was then pumped through the column at 30° C. at a rate of 86 ml/hour. Hydrolysis of the sucrose was determined polarimetrically. At the start, 27.5 g of sucrose were hydrolyzed per gram of carrier, charged with β-fructosidase, per hour. After 70 days, the carrier still had 57 percent of its initial immobilized activity.

EXAMPLE 3

0.2 g of the carrier used as in Example 2 was shaken in 20 ml of a solution containing 100 mg of β-amylase (28 international units/mg) in 0.05 M aqueous sodium acetate solution of pH 4.8 at 4° C. for 64 hours. The carrier was then washed at room temperature for two periods of 5 minutes and one period of 1 hour with in each case 50 ml of 0.05 M aqueous sodium acetate solution of pH 4.8. The carrier was shaken in 50 ml of a solution containing 5 g of Zulkowsky starch (Merck) in 0.016 M aqueous sodium acetate solution of pH 4.8 at 30° C. for 30 minutes in order to determine the immobilized enzymatic activity. The maltose formed was determined with 3,5-dinitrosalicylic acid by the method of P. Berenfeld (Methods in Enzymology, Volume 5, 149; Academic Press, 1955). The activity found was 1.1 g of maltose per gram of carrier per hour.

EXAMPLE 4

Amyloglycosidase was bound to the carrier in a manner similar to that in Example 3. The activity found was 0.6 g of glucose per gram of carrier per hour.

We claim:

1. A macroporous, hydrophilic enzyme carrier in bead form which comprises a polymer charged with polyethyleneimine, said polymer being sulfonated after its formation and containing sulfo groups polyethyleneimine being neither crosslinked nor covalently bonded to the polymer.

2. A carrier as claimed in claim 1, wherein the sulfo-containing polymer is a polymer, sulfonated after polymerization, of the following monomers:
   (a) from 10 to 100% by weight of divinylbenzene,
   (b) from 0 to 90% by weight of styrene, which may be mono-or polysubstituted by $C_1$-$C_4$-alkyl, and
   (c) from 0 to 20% by weight of monomers which are copolymerizable with styrene and divinylbenzene.

3. A carrier as claimed in claim 1, which has a pore volume of from 0.8 to 4 cm$^3$/g and a pore diameter of from $2.5 \times 10^{-5}$ to $2 \times 10^{-3}$ mm.

4. A carrier as claimed in claim 2, which has a pore volume of from 0.8 to 4 cm$^3$/g and a pore diameter of from $2.5 \times 10^{-5}$ to $2 \times 10^{-3}$ mm.

5. A carrier as claimed in claim 1, wherein the polyethyleneimine used has a molecular weight of from 1,000 to 5,000.

* * * * *

UNITED STATES PATENT AND TRADEMARK OFFICE
CERTIFICATE OF CORRECTION

PATENT NO. : 4,551,482
DATED : November 5, 1985
INVENTOR(S) : TSCHANG et al.

It is certified that error appears in the above—identified patent and that said Letters Patent is hereby corrected as shown below:

ON THE COVERING PAGE

The omission of the Foreign Application Priority Data was left out. Please insert:

[30]  Foreign Application Priority Data

June 22, 1982 [DE] Fed. Rep. of Germany.... 3223885.1

Signed and Sealed this

Eighteenth Day of February 1986

[SEAL]

Attest:

DONALD J. QUIGG

Attesting Officer

Commissioner of Patents and Trademarks